United States Patent [19]

Lowe et al.

[11] Patent Number: 4,489,062
[45] Date of Patent: Dec. 18, 1984

[54] PHARMACEUTICAL COMPOUNDS, PREPARATION, USE AND INTERMEDIATES THEREFOR AND THEIR PREPARATION

[76] Inventors: Lawrence A. Lowe, 38 Manse Way, Swanley, Kent; Terence W. Smith, 68 Maxwell Gardens, Orpington, Kent; Samuel Wilkinson, 12 Bevington Rd., Beckenham, Kent, all of England

[21] Appl. No.: 463,935

[22] Filed: Feb. 4, 1983

[30] Foreign Application Priority Data

Feb. 5, 1982 [GB] United Kingdom ............... 8203462

[51] Int. Cl.³ .................... A61K 37/00; C07C 103/52
[52] U.S. Cl. ............................ 424/177; 260/112.5 E
[58] Field of Search ................. 260/112.5 E; 424/177

[56] References Cited

U.S. PATENT DOCUMENTS

| | | | |
|---|---|---|---|
| 4,127,531 | 11/1978 | Coy et al. ...................... | 260/112.5 E |
| 4,127,534 | 11/1978 | Coy et al. ...................... | 260/112.5 E |
| 4,178,371 | 12/1979 | Morgan ......................... | 260/112.5 E |
| 4,213,968 | 7/1980 | Kastin et al. .................. | 260/112.5 E |
| 4,244,944 | 1/1981 | Wilkinson ...................... | 260/112.5 E |
| 4,254,106 | 3/1981 | Wilkinson ...................... | 260/112.5 E |
| 4,351,763 | 9/1982 | Gesellchen et al. ............. | 260/112.5 E |

*Primary Examiner*—Delbert R. Phillips
*Attorney, Agent, or Firm*—Donald Brown

[57] ABSTRACT

Novel peptides of formula (I)

$$X-Tyr-X^2-Gly-Phe(4NO_2)-Pro-NH_2 \qquad (I)$$

and salts thereof, wherein X is hydrogen or an amidino group and $X^2$ is a radical selected from D-S-methylmethionyl and D-arginyl, have a selectively peripheral analgesic effect when administered to mammals.

The compounds also exhibit antidiarrhoeal and antitussive activity and may thus be used in human or veterinary medicine for the relief or prevention of pain, for the treatment of diarrhoea or dysentery and for the suppression of cough.

8 Claims, No Drawings

PHARMACEUTICAL COMPOUNDS, PREPARATION, USE AND INTERMEDIATES THEREFOR AND THEIR PREPARATION

This invention relates to peptides useful in human and veterinary medicine, to the preparation of such compounds, to pharmaceutical formulations containing such compounds and the preparation of such formulations, to the use of the compounds in human and veterinary medicine and to intermediates for the said compounds and the preparation thereof.

The present invention more particularly relates to the novel peptides of formula (I)

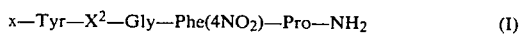

x—Tyr—$X^2$—Gly—Phe(4NO$_2$)—Pro—NH$_2$     (I)

as hereinafter defined which have been found to be of value in human and veterinary medicine in the prevention and relief of pain, that is to say, the said compounds are analgesics.

The safe and effective prevention and relief of pain has for long been the subject of investigation and enquiry and a number of analgesic agents are available to the physician and veterinarian. Such agents are recognized as producing this effect by either or both of two distinguishable mechanisms neither of which is yet fully understood. One such mechanism, giving rise to so-called central analgesis, is believed to involve receptors in the central nervous system (the brain and spinal cord) whilst the other, giving rise to the phenomenon of peripheral analgesia, is associated with events outside of these structures.

Agents having an effect with at least a substantial centrallymediated component include morphine, heroin and other of the opioids (see for example Goodman and Gilman's "*The Pharmacological Basis of Therapeutics*", sixth edition (1980), Macmillan Publishing Co., Inc. especially at Chapter 22, pages 494 to 534). Such compounds are valued for their efficacy in severe and often otherwise intractable pain, for example the pain of terminal illness such as cancer, postoperative pain and pain in parturition. As is well known however (Loc. cit., Chapter 23, pages 535 to 584) repeated administration of morphine et al. can lead to a physical dependence on the drug and tolerance to its actions and to withdrawal symptoms when administration is discontinued. Research has indicated that these aspects and the further side-effect of depression of respiration, all phenomena of the central nervous system, are intimately linked with analgesic potency.

Currently recognized peripheral analgesics however are non-opioid in character.

In 1975 Hughes et al. (*Nature*, 1975, 255, 577–579) reported the identification of two structurally related pentapeptides from the brain with potent opiate agonist activity, respectively named methionineenkephalin and leucine-enkephalin. Their properties and those of a large number of their analogues have since been investigated in detail and the picture has emerged of a class of compounds having a pharmacological spectrum very similar to that of the opioids. In particular it has been found that, allied to their analgesic action, the enkephalins have a physical dependence/tolerance potential (Wei, *J. Pharmacol. Exp. Ther.* 216:12–18, 1981), exhibit cross tolerance with opioids (Waterfield et al., *Nature*, 1976, 260, 624–625) and have a respiratory-depressant effect (Isom et al., *Pharmacologist* 21/3, 198 (1979)).

In direct contrast the analgesia induced by the peptides of formula (I) is sensibly only peripheral in origin. The compounds lack any significant degree of central analgesic activity and are especially advantageous in being without a respiratory-depressant effect and in having only a very low physical dependence/tolerance potential. These advantages and the specificity of action are together believed to be associated with the compounds' inability to cross the blood/brain barrier to any appreciable extent.

In formula (I), as set forth above,
X is hydrogen or an amidino group, and
$X^2$ is a radical selected from D-S-methylmethionyl and D-arginyl, together with salts thereof.

The abbreviations used herein for amino acids and their radicals are those conventional in the art and may be found in, for example, *Biochem. J.* (1972) 126, 773–780. In the above and throughout the following all references are to the L-configuration of chiral amino acids and their radicals unless otherwise stated.

As herein understood, the S-methylmethionyl radical is that having the structural formula

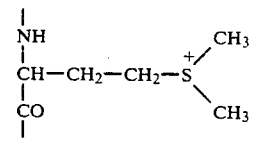

and the abbreviation -D-Met(ME)- indicates the D-configuration thereof.

Salts of the peptides of formula (I) include
acid addition salts, and
salts comprising the peptide as a cationic species (i.e. when $X^2$ is D-S-methylmethionyl) together with an anion.

In all such salts the biological activity resides in the peptide moiety and the identity of the other component is of less importance although for therapeutic purposes it is preferably pharmacologically acceptable to the recipient. Examples of pharmacologically acceptable acids include mineral acids such as hydrochloric, hydrobromic, phosphoric, metaphosphoric, nitric and sulphuric acids and organic acids such as tartaric, acetic, citric, malic, lactic, fumaric, benzoic, glycollic, gluconic, gulonic, succinic and arylsulphonic, for example p-toluenesulphonic, acids. Pharmacologically acceptable anions include those derived from the above-recited acceptable acids. The pharmacologically acceptable salts together with those salts which are not thus acceptable have utility in the isolation and/or the purification of the peptides per se, and of course the unacceptable salts are also valuable in being convertible to the acceptable salts by techniques well known in the art.

The analgesic properties of the peptides of formula (I) and in particular the selectively peripheral site of action thereof have been demonstrated by means of the following investigations.

(1) Both the hotplate test (Woolfe and MacDonald, *J. Pharmacol. Exp. Ther.* 80:300, 1944) and the irritant-induced writhing (stretch) test (Vander Wende and Margolin, *Fed. Proc.* 15:494, 1956) are standard in the art for the investigation of analgesic activity. Whereas it is believed that the pain in the latter can be ameliorated either centrally or peripherally, it is thought that that induced in the hotplate test is affected only at the central level. When tested by modifications of these literature procedures the peptides are considerably more potent in the writhing test than in the hotplate test on parenteral (i.e. peripheral) administration, that is to say a lower dose of the compound is required to provide a given reduction in the reaction to the test stimulus, indicating a peripheral site of action.

(2) The respective time courses of the analgesia induced by the peptides in the hotplate and writhing tests, upon peripheral (parenteral) administration, indicate that the compounds penetrate the blood-brain barrier comparatively slowly and to only a very limited extent.

(3) The analgesia induced by the peptides in the writhing test upon peripheral (parenteral) administration is antagonised by parenteral administration of the quaternary opioid antagonist N-allyl-normorphine methiodide (N-methylnalorphine; Koczka et al, *Acta Chim. Acad. Sci. Hung.* 51:393, 1967), i.e. a higher dose of the peptide is required in the presence than in the absence of the opioid for the same effect. As penetration of the blood-brain barrier by the quaternary compound is minimal (c.f. Tavani et al, *European J. Pharmacol.* 59:151-154, 1979) both the peptide-induced analgesia and the antagonism thereof are effected at the peripheral level.

The peptides of formula (I) and the salts thereof may be prepared by those methods known in the art for the synthesis of compounds of analogous structure and in this regard reference is made, by way of illustration only, to the following literature.

(a) Schröder and Lüebke, "*The Peptides*" (Academic Press, 1965).
(b) Stewart and Young, "*Solid Phase Peptide Synthesis*" (W. H. Freeman and Co., 1969).
(c) Bellean and Malek, *J. Am. Chem. Soc.* 90:165, 1968).
(d) Beyerman, *Helv. Chim. Acta* 56:1729, 1973.
(e) Tilak, *Tetrahedron Letters* 849 (1970).

All references identified hereinabove or in the following are hereby incorporated herein by reference thereto.

(1) In one such preparative approach the peptides and salts are formed by the sequential coupling of appropriate amino acids using either classical methods of peptide synthesis or solid phase procedures, or by the initial preparation and subsequent coupling of peptide subunits. Such reactions may be effected by, for example, activating the reacting carboxyl group of the ingoing amino acid and protecting the non-reacting amino and carboxyl groups, and details of suitable activating and protecting (masking) groups and of suitable reaction conditions (both for the coupling reactions and for the removal of protecting groups) giving the minimum of racemisation may be found in the above-referenced literature.

The peptides and salts may thus be prepared by reacting a reagent (II)

X—Y$^1$—OH                (II)

wherein X has the meaning as hereinabove recited and Y$^1$ is a partial radical sequence identical with the corresponding N-terminal partial radical sequence in formula (I), with a reagent (III)

H—Y$^2$—NH$_2$            (III)

wherein Y$^2$ is a partial radical sequence identical with that in the balance of the above-defined product peptide, the reagents (II) and (III) being optionally protected and/or activated where and as appropriate; followed as appropriate by deprotection of the product.

(2) As another possibility the peptides and salts may be prepared by reacting with ammonia an appropriate peptide ester (IV)

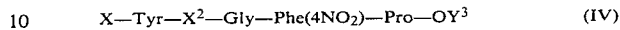

X—Tyr—X$^2$—Gly—Phe(4NO$_2$)—Pro—OY$^3$    (IV)

wherein X and X$^2$ have the meanings as hereinabove recited and Y$^3$ is for example an alkyl group and preferably an alkyl group of 1 to 4 carbon atoms, i.e. methyl, ethyl, propyl or butyl.

(3) As a further method the peptides and salts may be prepared by appropriate treatment of a peptide (V)

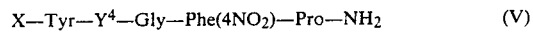

X—Tyr—Y$^4$—Gly—Phe(4NO$_2$)—Pro—NH$_2$   (V)

wherein X has the meaning as hereinabove recited and Y$^4$ is the radical of a D-amino acid that is convertible to respectively the D-S-methylmethionyl or D-arginyl radical.

The peptides(I) and salts thereof wherein X$^2$ is D-S-methylmethionyl may thus be prepared by S-methylation of ((V), Y$^4$ is D-methionyl) using a conventional methylating agent such as methyl iodine, while the peptides (I) and salts thereof wherein X$^2$ is D-arginyl may be prepared by guanidation of ((V), Y$^4$ is D-ornithyl) using a reagent such as 1-guanyl-3,5-dimethylpyrazole.

The esters (IV) and the peptides (V) may themselves be prepared by standard techniques analogous to those described under (1) supra.

The peptides of formula (I) may be isolated as the compounds per se or as salts thereof and it will be appreciated that the said compounds may be converted to salts thereof, and the reverse, and the salts converted to other salts, by techniques well-known and conventional in the art.

The peptides of formula (I) and the pharmacologically acceptable salts thereof may be used in both human and veterinary medicine for the prevention and relief of pain. Specific indications, by way of example only, include pain arising from soft tissue injury, pain in the post-surgical period, pain in parturition and post-partum, pain in dysmenorrhoea, neuralgia, myalgia, pain in arthritis and rheumatic conditions and that of musculoskeletal conditions in general.

The peptides and salts thereof may be administered to the human or nonhuman recipient by a route selected from oral, parenteral (including subcutaneous, intradermal, intramuscular and intravenous), rectal and topical (including dermal, buccal and sublingual). The size of an effective analgesic dose of a compound will depend upon a number of factors including the identity of the recipient, the severity of the pain involved and the route of administration and will ultimately be at the discretion of the attendant physician or veterinarian although, in view of the subjective nature of the desired end result, self-administration by a human recipient may be acceptable in some circumstances. An effective dose for a human being will generally be in the range 5 to 500 mg., more generally in the range 10 to 250 mg. and most often in the range 20 to 125 mg., a particularly suitable dose being 50 mg. (all doses calculated as the peptide per se : for salts the figures would be adjusted proportionately). Administration of such doses may be repeated as required throughout the day, for example three or four times a day. For veterinary use, for example in the treatment of non-human mammals such as cats, dogs, cattle, sheep, pigs and horses, the above-recited doses would be increased or decreased at the discretion of the veterinarian having regard to the weight and identity of the recipient.

While it is possible for the compounds to be administered as the raw chemical it is preferable to present them as a pharmaceutical formulation preparation. The formulations of the present invention comprise a peptide of formula (I), as above defined, or a pharmacologically acceptable salt thereof together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous), rectal and topical (including dermal, buccal and sublingual) administration although the most suitable route may depend upon for example the condition and identity of the recipient. The formulations may conveniently be presented in unit dosage form and may be prepared by any of the methods well known in the art of pharmacy. All methods include the step of bringing into association the peptide or salt (the active ingredient) with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or pasta.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinabove recited, or an appropriate fraction thereof, of the active ingredient.

Formulations for topical administration to the skin, i.e. dermally, may be presented in anhydrous forms such as ointments, lotions, pastes, jellies, sprays, aerosols and bath oils. The term ointment includes formulations (including creams) having oleaginous, absorption, water-soluble and emulsion type bases, for example petrolatum, lanolin, polyethylene glycols and mixtures thereof. Such formulations are particularly valuable for use in the prevention and relief of localised pain, for example that arising in arthritis and rheumatic conditions, and may be applied to the desired area one or more times daily as required; they conveniently contain the compound in a concentration in the range 0.05 to 2% w/w, preferably in the range 0.1 to 1% w/w and most preferably in the range 0.2 to 0.5% w/w, calculated as the peptide per se.

It should be understood that in addition to the ingredients particularly mentioned above the formulations of this invention may include other agents conventional in the art having regard to the type of formulation in question, for example those suitable for oral administration may include flavouring agents.

In addition to the analgesic properties hereinabove described the peptides of formula (I) and their salts have been found to exhibit (a) antidiarrhoeal and (b) antitussive activity when investigated according to standard pharmacological procedures and may thus also be used, in both human and veterinary medicine, in the treatment of diarrhoea and dysentery and in the suppression of cough. For each of these further utilities the compounds may be administered to the recipient by the same routes, at the same doses and as the same pharmaceutical formulations as hereinabove described in respect of their use in the prevention and relief of pain although it will be appreciated that the size of an effective dose will again depend upon the same general considerations as indicated hereinbefore, namely, the identity of the recipient, the condition involved and its severity and the route of administration, and that the most suitable route may depend for example upon the condition and the recipient.

Further to the methods hereinbefore described it will be appreciated that the peptides of formula (I) and salts thereof wherein X is an amidino group may also be prepared by (4) reaction of the corresponding peptide wherein X is hydrogen with a reagent such as 1-amidino-3,5-dimethylpyrazole.

It will be understood from the foregoing description that this invention may comprise any novel feature described herein, principally but not exclusively for example:

(a) Peptides of formula (I) as hereinbefore defined and salts thereof.

(b) Methods as hereinbefore described for the preparation of compounds according to (a) supra, together with the compounds when so prepared.

(c) Peptides of formula (I) as hereinbefore defined and pharmacologically acceptable salts thereof, for use in the medical treatment of a mammal, for example a human being.

(d) Peptides of formula (I) as hereinbefore defined and pharmacologically acceptable salts thereof, for use as an analgesic agent.

(e) A pharmaceutical formulation comprising an analgesic amount of a peptide of formula (I) as hereinbefore defined or a pharmacologically acceptable salt thereof together with an acceptable carrier therefor.

(f) A method for the relief or prevention of pain in a mammal comprising administering to a mammal, for example a human being, in or about to suffer pain a non-toxic, analgesic amount of a peptide of formula (I) as hereinbefore defined or a pharmacologically acceptable salt thereof.

(g) Peptides of formula (I) as hereinbefore defined and pharmacologically acceptable salts thereof, for use as an antidiarrhoeal, antidysentery or antitussive agent.

(h) A pharmaceutical formulation comprising an antidiarrhoeal, antidysentery or antitussive amount of a peptide of formula (I) as hereinbefore defined or a pharmacologically acceptable salt thereof together with an acceptable carrier therefor.

(i) A method for the treatment of diarrhoea or dysentery or for the suppression of cough in a mammal for example a human being comprising administering to said mammal a non-toxic, effective amount of a peptide of formula (I) as hereinbefore defined or a pharmacologically acceptable salt thereof.

(j) Novel compounds of formulae (II) to (V) as hereinbefore defined, methods for their preparation as hereinbefore described and the compounds when so prepared.

The following Examples are provided in illustration of the present invention and should not be construed as in any way constituting a limitation thereof. All temperatures are in degrees Celsius.

| Experimental | | |
|---|---|---|
| Abbreviations | DMF | dimethylformamide |
| | THF | tetrahydrofuran |
| | DCCI | dicyclohexylcarbodiimide |
| | HOBT | 1-hydroxybenzotriazole |
| | NMM | N—methyl morpholine |
| T.l.c. (Merck silica gel plates) with the solvent systems | | |
| sI | n-butanol/acetic acid/water (3:1:1) (by vol.) | |
| sII | methylethylketone | |
| sIII | chloroform/methanol/32% aq. acetic acid (120:90:5) (by vol.) | |
| sIV | chloroform/methanol (8:1) (by vol.) | |
| sV | chloroform/methanol/880 ammonia (120:90:5) (by vol.) | |
| sVI | chloroform/methanol/32% aq. acetic acid (120:90:40) (by vol.) | |
| sVII | chloroform/methanol/.880 ammonia (120:90:40) (by vol.) | |

H—Gly—Phe(4—NO₂)—Pro.NH₂

The common intermediate tripeptide was prepared as illustrated in Scheme I and the experimental details are given below.

SCHEME I

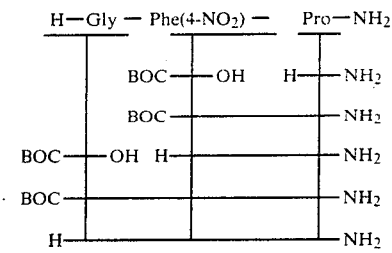

BOC—Phe(4—NO₂)—Pro.NH₂

BOC—Phe(4—NO₂) (33.4 g) was dissolved in DMF (350 ml), HOBT (29.1 g) was added, and the mixture cooled to −10° C. DCCI (22.2 g) was added with stirring and maintained at −5° C. for 30 minutes. After the addition of Pro—NH₂.HCl (16.2 g) and NMM (10.9 g) the reaction mixture was stirred at 4° C. for 24 hours. The product was filtered to remove dicyclohexylurea and solvent removed in vacuo at 35° C. The residual oil was taken up in ethyl acetate (1500 ml), filtered and the filtrate was washed with 250 ml ½ sat. sodium choride solution, 2×250 ml 5% citric acid solution, 4×250 ml 5% sodium bicarbonate solution, and finally 2×250 ml ½ sat. sodium chloride solution. The ethyl acetate extract was dried over anhydrous magnesium sulphate and concentrated to dryness. The residual white solid was warmed with ethyl acetate (300 ml) and diluted with ether (400 ml). After refrigeration the product was collected by filtration, washed with ether and dried.

Yield 38.0 g (87%) m.p. 182.5°-184° C. $[\alpha]_D^{20}$ −28.0° (c = 1, MeOH) $[\alpha]_{546}^{20}$ −32.5° (c = 1, MeOH) Calc. for $C_{19}H_{26}N_4O_6$: C, 56.16; H, 6.40; N, 13.79. Found: C, 56.92; H, 6.85; N, 13.42%. T.l.c.: indicates a trace of dicyclohexylurea present.

H—Phe(4—NO₂)—Pro.NH₂ hydrochloride

A solution of 1M.HCl in glacial acetic acid (600 ml) was cooled to 10° C. and BOC—Phe(4—NO₂)—Pro.NH₂ (53.5 g) was added with stirring. The solid dissolved initially and precipitation occurred after 15 minutes. After a total reaction time of 40 minutes the solvent was removed in vacuo at 30° C. and the residue was triturated with dry ether. The crude product was crystallised from ethanol/isopropanol.

Yield 39.8 g (88%), M.p. 192°-194° C. (decomp.). $[\alpha]_D^{26}$ −15.0° (c = 1, MeOH) $[\alpha]_{546}^{26}$ −17.4° (c = 1, MeOH)

BOC—Gly—Phe(4—NO₂)—Pro.NH₂

BOC—Gly (22.36 g) in THF (200 ml) was cooled to −25° C. and treated with NMM (12.91 g). A solution of isobutyl chloroformate (16.65 g) in THF (50 ml) was added over 1 minute with vigorous stirring. During the addition the temperature rose to −15° C. After a further 2 minutes, a pre-cooled (−30° C.) solution of Phe(-4—NO₂)—Pro.NH₂.HCl (3908 g) and NMM (11.74 g) in DMF (150 ml) was added and the mixture was stirred at −15° C. for 3 hours. The reaction vessel was then transferred to an icebath, 2M potassium bicarbonate (130 ml) added and stirring continued for 30 min. Solvents were removed in vacuo and the residual oil was partitioned between ethyl acetate (1500 ml) and ¼ sat.

sodium chloride solution (250 ml). The organic phase was washed with 3×350 ml 5% citric acid solution, 3×250 ml 5% sodium bicarbonate solution and 2×250 ml ½ sat. sodium chloride, dried (MgSO$_4$) and concentrated to a solid foam which was triturated with light petroleum.

Yield 44.4 g (83%). Pure by T.l.c. SI, SIII, SV.

H—Gly—Phe(4—NO$_2$)—Pro.NH$_2$ hydrochloride

The protected tripeptide (44.4 g) was dissolved in glacial acetic acid (250 ml) and treated with 2M HCl in acetic acid (250 ml) for 30 minutes at room temperature. The solvent was removed in vacuo at 30° C. and the residue triturated with dry ether. The crude product was precipitated from hot ethanol (275 ml) by the slow addition of isopropanol (150 ml) followed by isopropyl ether (100 ml). After refrigeration the solid was filtered and washed with isopropyl ether.

Yield 35.95 g (93.8%). Essentially pure by T.l.c. SI, SIII, SV. $[\alpha]_D^{24}$ −14.5° (c=1, MeOH). $[\alpha]_{546}^{24}$ −15.9° (c=1, MeOH).

EXAMPLE 1

H—Tyr—D—Arg—Gly—Phe(4—NO$_2$)—Pro.NH$_2$ diacetate

SCHEME 2

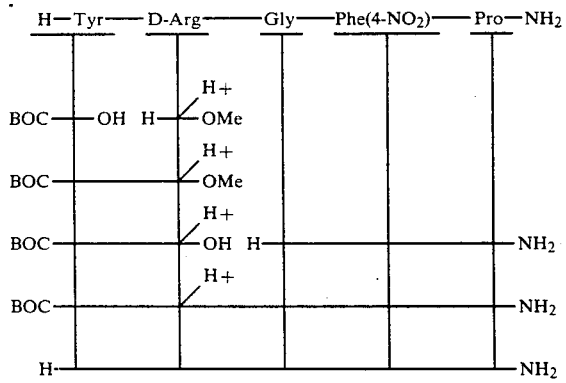

BOC—Tyr—D—Arg—OMe

To BOC-Tyr (1.184 g) in THF (20 ml) was added NMM (0.426 g) in THF (5 ml). The mixture was cooled to −25° C. and treated with isobutylchloroformate (0.549 g) in THF (5 ml) and allowed to react at −15° C. for 2 minutes. A precooled solution of D—Arg—OMe.2HCl (1.0 g) and NMM (0.387 g) in DMF (20 ml) and water (2 ml) was added and the mixture was stirred at −15° C. for 2.5 hours. 2M KHCO$_3$ (4.6 ml) added and stirred at 0° C. for 30 min. Solvents were removed in vacuo, and the residue distributed between ethyl acetate and water. The organic phase was washed twice with water. The combined aqueous extracts were adjusted to pH 7 by the addition of acetic acid and after saturation with salt, extracted with chloroform/butanol 5:1 and then twice with chloroform. The combined organic layers were washed twice with sat. salt solution, dried (MgSO$_4$) and concentrated in vacuo. The residue was triturated with dry ether.

Yield 1.28 g (74%).

BOC—Tyr—D—Arg hydrochloride

The protected dipeptide (1.28 g) was dissolved in methanol (40 ml) and water (10 ml). M NaOH (5.7 ml) was added and the mixture stirred at room temperature for 3½ hours, then neutralised by the addition of M HCl (5.7 ml). The methanol was removed in vacuo and the residual aqueous solution was freeze dried.

A solution of the crude product in water was desalted by absorption onto a Zorbax C-8 column and subsequent elution using a methanol gradient. The isolated dipeptide was dissolved in water, treated with one equivalent of M HCl and freeze dried.

Yield 0.78 g (58%). Calc. for C$_{20}$H$_{31}$N$_5$O$_6$.HCl.2-H$_2$O: C, 48.83; H, 6.91; N, 14.24. Found: C, 49.06; H, 6.79; N, 13.73%. Single spot on T.l.c. in SI, SIII, SV.

BOC—Tyr—D—Arg—Gly—Phe(4—NO$_2$)—Pro.NH$_2$

To BOC—Tyr—D—Arg.HCl (0.78 g) in DMF (25 ml) was added HOBT (0.446 g). With cooling to −10° C., DCCI (0.340 g) was added. After stirring at −5° C. for 30 minutes, Gly—Phe(4-NO$_2$)—Pro.NH$_2$.HCl (0.659 g) and NMM (0.167 g) were added and the mixture was stirred at 4° C. for 72 hours.

Dicyclohexylurea was removed by filtration, and the filtrate was concentrated in vacuo. The crude product was distributed between ethyl acetate and water. The aqueous phase was saturated with salt and extracted thoroughly with a mixture of ethyl acetate and butanol (10:1). The organic layer was washed once with a small volume of water and then concentrated. Re-evaporation from ethanol (2 x) and trituration with ether gave the title compound.

H—Tyr—D—Arg—Gly—Phe(4—NO$_2$)—Pro.NH$_2$ diacetate

The protected pentapeptide (0.94 g) was suspended in anisole (15.5 ml) and treated with M HCl/HOAc (44 ml). After 1 hour at room temperature, solvent was removed in vacuo and the residue triturated with dry ether. The crude product was purified by ion-exchange chromatography on carboxymethyl cellulose. Elution with a linear gradient of ammonium acetate and repeated freeze drying gave the pure pentapeptide diacetate.

T.l.c.: Pure in SI, SIII, SV. Calc. for C$_{31}$H$_{42}$N$_{10}$O$_8$2-HAc.2H$_2$O: C, 50.12; H, 6.44; N, 16.71. Found: C, 50.33; H, 6.50; N, 16.84%.

EXAMPLE 2

H—Tyr—D—Met(Me)—Gly—Phe(4NO$_2$)—Pro.NH$_2$ chloride, hydrochloride

H—Tyr—D—Met—Gly—Phe(4NO$_2$)—Pro.NH$_2$ hydrochloride (12.76 mmole), prepared in the manner described in Example 1 of GB-A 1 604 850, was dissolved in methanol (250 ml) and treated with methyl iodide (7.75 ml). The reaction mixture was protected from light and kept at room temperature. After 2 days further methyl iodide (7.75 ml) was added. After a total of 5 days the reaction mixture was concentrated in vacuo and purified by fractionation on carboxymethylcellulose, using a linear gradient of ammonium acetate. The purified product was isolated as the chloride, hydrochloride.

Calc. for C$_{31}$H$_{43}$N$_7$O$_8$SCl$_2$.3H$_2$O: C, 46.66; H, 6.14; N, 12.28. Found: C, 47.09; H, 6.02; N, 12.12%.

Characterising data for the compounds of the foregoing Examples are as follows

|  |  | Ex. 1 | Ex. 2 |
|---|---|---|---|
| $[\alpha]_D^{26.5}$ | (c = 1, methanol) | +12.0° | — |
| $[\alpha]_{546}^{26.5}$ | (c = 1, methanol) | +14.7° | — |
| $[\alpha]_D^{21}$ | (c = 1, methanol) | — | +15.8° |
| $[\alpha]_{546}^{21}$ | (c = 1, methanol) | — | +19.6° |
| T.l.c. Rf | SI | 0.14 | 0.15 |
|  | SVI | 0.42 | 0.40 |
|  | SVII | 0.22 | 0.05 |

EXAMPLE 3

N—AmidinoTyr—D—Arg—Gly—Phe(4—NO₂)—Pro.NH₂ diacetate

The diacetate product of Example 1 (500 mg) was dissolved in a mixture of ethanol (2 ml) and DMF (0.5 ml). 1-Amidino-3,5-dimethylpyrazole acetate (150 mg) and triethylamine (0.12 ml) were added to the solution and the mixture stirred at 55° C. for 6 hr. and then at room temperature overnight. The mixture was concentrated in vacuo and the residue triturated with ethyl acetate. The resulting crude material was chromatographed on a column of carboxymethylcellulose with elution by a linear gradient of ammonium acetate, pH 5-1 (0.005 M →0.5 M). Fractions containing the pure product were combined and freeze-dried three times to remove volatile buffer.

T.l.c.: Pure in SI, SII, SIII and by HPLC. Calculated for $C_{32}H_{44}N_{12}O_8.2CH_3CO_2H.2H_2O$: C, 49.09; H, 6.36; N, 19.09. Found: C, 49.34; H, 6.47; N, 19.15.

EXAMPLE 4

N—AmidinoTyr—D—Met(Me)—Gly—Phe(4NO₂)—Pro.NH₂ chloride, hydrochloride

The chloride, hydrochloride product of Example 2 (1.0 g) was dissolved in ethanol (5 ml) and treated with 1-amidino-3,5-dimethylpyrazole acetate (0.33 g) and triethylamine (0.30 ml). The mixture was heated to 60° C. for 4 hr. and then stirred at room temperature overnight and the residue obtained after solvent removal triturated with ethyl acetate. The crude product was purified on carboxymethylcellulose as in Example 3 and then converted to the chloride, hydrochloride by treatment with M HCl.

Calculated for $C_{32}H_{44}N_9O_8SCl.HCl.4H_2O$: C, 44.75; H, 6.18; N, 14.68. Found: C, 44.66; H, 5.97; N, 14.43.

EXAMPLE 5

Pharmacological Results (A) Hotplate test

Male mice (CFLP strain, Hacking and Churchill) were individually placed in a copper-bottomed perspex box suspended in a water bath at 55° C. and observed for signs of discomfort such as shaking or licking the paws, the reaction time (up to a maximum of 30 secs.) being recorded. Groups of five animals then received either a test compound or saline vehicle (0.85%) control by subcutaneous injection, the test being repeated at 15 mins. after treatment. The ED₅₀ figures for the test compounds were calculated from the number of animals having a posttreatment reaction time which was twice the pretreatment figure.

| Compound | $ED_{50}$ (mg/kg, s.c.) |
|---|---|
| Ex. 1 | 94.8* |
| Ex. 2 | 129.5* |
| Indomethacin | No effect at 100 |
| Pentazocine | No effect at 100 |
| Dextropropoxyphene | 25.9 |
| Morphine | 1.8 |
| Ex. 3 | No effect at 25* |
| Ex. 4 | 43.8* |

*calculated as the peptide per se (B) Irritant-induced writhing test (i) Acetic Acid. Groups of five female CD1 mice (Charles River) received either a test compound or saline vehicle (0.85%) control by subcutaneous injection 15 mins. (unless otherwise indicated) prior to an intraperitoneal injection of 0.6% acetic acid at a dose volume of 25 ml/kg. After a further 20 mins. the writhing or stretching movements induced by the irritant were counted over a 2½ min. period, a writhe/stretch being identified as an extension of a hindlimb accompanied by constriction of the abdomen.

(ii) Phenylbenzoquinone (PBQ). This test was carried out in a parallel manner to that employing acetic acid, except acid, except that the period over which the writhing/stretching movements were counted began 10 mins. after administration of the PBQ irritant, the latter being given at a dosage of 2.5 mg/kg and in a dose volume of 10 ml/kg.

The ED₅₀ figures for the test compounds were calculated, using linear regression analysis, as the dose in the presence of which only half the number of writhes/stretches was induced compared with the controls.

| Compound | $ED_{50}$ (mg/kg, s.c.) | |
|---|---|---|
|  | Acetic acid | PBQ |
| Ex. 1 | **4.3 | **4.0 |
| Ex. 2 | **1.2 | **4.6 |
| Indomethacin |  | 0.9 |
| Pentazocine | 2.3 |  |
| Dextropropoxyphene | 4.2 | 2.6 |
| Morphine | 0.45* | 0.38 |
| Ex. 3 | **1.2 | **1.3* |
| Ex. 4 | **0.6 | **1.0 |

*compound administered 30 mins. prior to acetic acid/PBQ
**calculated as the peptide per se (C) Antagonism by quaternary opioid Groups of six male TFW mice (Tuck) received by intraperitoneal injection either N-methylnalorphine (16 mg/kg) or saline vehicle (0.85%) control at a volume of 10 ml/kg followed after 20 mins. by a solution of the test compound in saline (10 ml/kg, subcutaneous) and after a further 30 mins. by 0.6% acetic acid (25 ml/kg, intraperitoneal). The total number of writhes/stretches per group was then determined over the 5 min. period commencing 15 mins. after administration of the acetic acid. Using linear regression analysis the ED₅₀ figures for the test compounds were calculated (defined as in (B) supra) together with the dose ratios therefor, i.e. the ratios of the dose of compound required for equiactive antinociceptive effect in respectively the presence and the absence of the quaternary compound.

| Compound | ED$_{50}$ (mg/kg, s.c.) | | Dose ratio (a):(b)* |
|---|---|---|---|
| | N—methyl-nalorphine (a) | Saline control (b) | |
| Ex. 1 | **18.7 | **4.6 | 4.1 |
| Ex. 2 | **4.1 | **1.5 | 3.3 |
| Dextropropoxyphene | 6.9 | 6.8 | 1.0 |
| Morphine | 0.24 | 0.4 | 0.9 |
| Ex. 3 | **2.1 | **0.5 | 4.6 |
| Ex. 4 | **1.7 | **0.7 | 4.2 |

*calculated from the linear regression of the respective dose/response curves
**calculated as the peptide per se (D) Antidiarrhoeal activity Female Cobs Wistar rats (Charles River) were starved for 24 hours prior to subcutaneous administration of the test compound as a solution in 0.85% (w/w) saline and at a volume of 10 ml/kg. Fifteen minutes after the compound each rat received 1 ml. castor oil given orally and the animals were then observed for the appearance of diarrhoea. The ED$_{50}$s for each compound, calculated as the dose required to suppress diarrhoea in 50% of the animals, were derived from the results obtained at various intervals post castor oil.

| Compound | **ED$_{50}$ (mg/kg, s.c.) | | |
|---|---|---|---|
| | 1.5 hrs.* | 2.0 hrs.* | 3.0 hrs.* |
| Ex. 1 | 0.79 | 3.19 | 54.9 |
| Ex. 2 | 0.16 | 0.89 | 8.61 |
| Ex. 4 | 0.07 | 0.14 | 0.84 |

*post castor oil
**calculated as the peptide per se (E) Antitussive activity

In this test procedure, a modification of that described by Boura et al., Br. J. Pharmac., 39/1 (1970) 225, guinea pigs were subjected to an aerosol containing 30% citric acid, 30 minutes after subcutaneous administration of test compound as a solution in 0.85% (w/w) saline, and the number of coughs during a 12½-minute exposure counted.

Based on linear regression analysis the ED$_{50}$ (the dose required to reduce the number of coughs by 50% compared with saline-treated controls) for the compound of Example 1 was 0.26 mg/kg, calculated as the peptide per se (95% confidence limits: 0.04–2.6 mg/kg).

(F) Toxicology

The diacetate product of Example 1 was administered subcutaneously to rats and marmosets as a solution in 0.85% (w/w) saline at a volume of 0.1 ml/100 g bodyweight. For each species the compound was given daily for 14 days at a dose (calculated as the peptide per se) selected from 7.5, 15 and 30 mg/kg bodyweight per day.

In marmosets the only clinical signs observed were transient post-dose vomiting and salivation at 30 mg/kg and to a lesser extent at the lower doses.

No toxicity attributable to the compound was seen in the rat.

EXAMPLE 6

Pharmaceutical formulations

| (A) Tablet | |
|---|---|
| Compound of formula (I) (calculated as peptide per se) | 50 mg |
| Lactose | 76 mg |
| Maize starch | 10 mg |
| Gelatin | 2 mg |
| Magnesium stearate | 2 mg |

Mix together the compound of formula (I), lactose and maize starch. Granulate with a solution of the gelatin dissolved in water. Dry the granules, add the magnesium stearate and compress to produce tablets each containing 50 mg of compound, calculated as peptide per se.

| (B) Suppository | |
|---|---|
| Compound of formula (I) (calculated as peptide per se) | 2.5 g |
| Suppository base (Massa Esterinum C) | to 100 g |

Melt the suppository base at 40° C. Gradually incorporate the compound of formula (I) in fine powder form and mix until homogeneous. Pour into suitable moulds, 2 g per mould, and allow to set.

Massa Esterinum C is a commercially available suppository base (Henkel International, Dusseldorf) consisting of a mixture of mono-, di- and triglycerides of saturated vegetable fatty acids.

| (C) Freeze-dried injection | |
|---|---|
| Compound of formula (I) (calculated as peptide per se) | 50 mg |
| Water for injections | to 2.0 ml |

Dissolve the compound of formula (I) in the water for injections. Sterilise the solution by passage through a membrane filter, 0.2 μm pore size, collecting the filtrate in a sterile receiver. Fill into sterile glass vials, 2 ml/vial under aseptic conditions and freeze-dry. Close the vials with sterile rubber closures secured with an aluminium seal.

The injection is reconstituted prior to administration by the addition of a convenient volume of water for injections or sterile saline solution.

| (D) Capsule | |
|---|---|
| Compound of formula (I) (calculated as peptide per se) | 50 mg |
| Starch 1500 | 150 mg |
| Magnesium stearate | 1 g |

Mix the ingredients and fill into hard gelatin capsules, each to contain 50 mg of compound calculated as peptide per se.

What we claim is:

1. A peptide of formula (I)

X—Tyr—X$^2$—Gly—Phe(4NO$_2$)—Pro—NH$_2$    (I)

or a pharmacologically acceptable salt thereof wherein
X is hydrogen or an amidino group, and
X$^2$ is a radical selected from D—S—methylmethionyl and D—arginyl.

2. A peptide according to claim 1 or a pharmacologically acceptable salt thereof wherein X is hydrogen.

3. A compound according to claim 1 which is

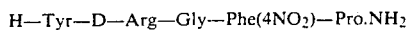

or a pharmacologically acceptable salt thereof.

4. A pharmaceutical formulation comprising a peptide according to any of claims 1 to 3, or a pharmacologically acceptable salt thereof, together with an acceptable carrier therefor.

5. A method for the relief or prevention of pain in a mammal comprising administering to said mammal a non-toxic, analgesic amount of a peptide according to any of claims 1 to 3 or a pharmacologically acceptable salt thereof.

6. A method for the treatment of diarrhoea or dysentery in a mammal comprising administering to said mammal a non-toxic, effective amount of a peptide according to any of claims 1 to 3 or a pharmacologically acceptable salt thereof.

7. A method for the suppression of cough in a mammal comprising administering to said mammal a non-toxic, effective amount of a peptide according to any of claims 1 to 3 or a pharmacologically acceptable salt thereof.

8. The method of providing peripheral analgesia in a mammal suffering from pain which comprises administering to a mammal an effective amount of the compound of pharmacologically acceptable salt of claims 1, 2, or 3.

9. A pharmacologically acceptable salt of a peptide of claims 1, 2 or 3.

* * * * *